United States Patent
Schultz

(10) Patent No.: US 8,808,248 B2
(45) Date of Patent: Aug. 19, 2014

(54) CATHETER SHEATH INTRODUCER WITH ROTATIONAL LOCK

(75) Inventor: Jeffrey William Schultz, Chino, CA (US)

(73) Assignee: Biosense Webster, Inc., Diamond Bar, CA (US)

( * ) Notice: Subject to any disclaimer, the term of this patent is extended or adjusted under 35 U.S.C. 154(b) by 121 days.

(21) Appl. No.: 12/580,001

(22) Filed: Oct. 15, 2009

(65) Prior Publication Data

US 2011/0092910 A1    Apr. 21, 2011

(51) Int. Cl.
- *A61M 5/178* (2006.01)
- *A61B 17/34* (2006.01)
- *A61M 25/00* (2006.01)

(52) U.S. Cl.
CPC ....... *A61B 17/3462* (2013.01); *A61B 2017/345* (2013.01); *A61M 25/0097* (2013.01)
USPC ............. 604/165.01; 604/164.01; 604/167.01

(58) Field of Classification Search
CPC ........... A61B 17/3462; A61B 17/3464; A61B 2017/347; A61M 25/0097; A61M 25/013; A61M 25/0606
USPC ............. 604/165.01–165.04, 167.01, 167.06, 604/167.03, 164.01
See application file for complete search history.

(56) References Cited

U.S. PATENT DOCUMENTS

| | | | |
|---|---|---|---|
| 3,789,852 A * | 2/1974 | Kim et al. ...................... | 604/104 |
| 5,279,597 A | 1/1994 | Dassa et al. | |
| 5,466,230 A | 11/1995 | Davila | |
| 5,807,350 A | 9/1998 | Diaz | |
| 5,964,740 A | 10/1999 | Ouchi | |
| 6,645,176 B1 * | 11/2003 | Christenson et al. ......... | 604/151 |
| 6,802,835 B2 | 10/2004 | Rabiner et al. | |
| 7,179,252 B2 | 2/2007 | Agro et al. | |
| 7,914,491 B2 * | 3/2011 | Rockrohr ................. | 604/164.01 |
| 2002/0072713 A1 * | 6/2002 | Almond et al. .......... | 604/167.05 |
| 2005/0060016 A1 | 3/2005 | Wu et al. | |
| 2005/0070820 A1 | 3/2005 | Boutillette et al. | |
| 2005/0070851 A1 * | 3/2005 | Thompson et al. ...... | 604/167.03 |
| 2005/0277909 A1 | 12/2005 | McDaniel | |
| 2006/0041270 A1 | 2/2006 | Lenker et al. | |
| 2009/0209913 A1 * | 8/2009 | Ferrari ..................... | 604/165.04 |
| 2009/0326463 A1 * | 12/2009 | Ross ........................ | 604/167.01 |

FOREIGN PATENT DOCUMENTS

| | | |
|---|---|---|
| EP | 0 648 470 A1 | 4/1995 |
| GB | 330629 | * 12/1930 |
| GB | 330629 A | * 12/1930 |
| WO | WO 01/89397 A1 | 11/2001 |
| WO | WO 2004/110286 A1 | 12/2004 |
| WO | WO 2006117819 A1 | * 11/2006 |

OTHER PUBLICATIONS

International Search Report (completed Jan. 13, 2011) mailed Jan. 26, 2011 for EP Application No. 10251800.8, 8 pgs.

* cited by examiner

*Primary Examiner* — Quynh-Nhu H Vu
*Assistant Examiner* — Jenna Zhang
(74) *Attorney, Agent, or Firm* — Christie, Parker & Hale, LLP

(57) ABSTRACT

A sheath introducer for use with a catheter, has a hub and a tube through which the catheter extends, and a lock assembly which has a rotational knob that actuates a plurality of prongs arranged in a radial pattern around a hole in the hub that receives the catheter, wherein the prongs synchronously rotate in one direction to grip the catheter or in the other direction to release the catheter.

20 Claims, 7 Drawing Sheets

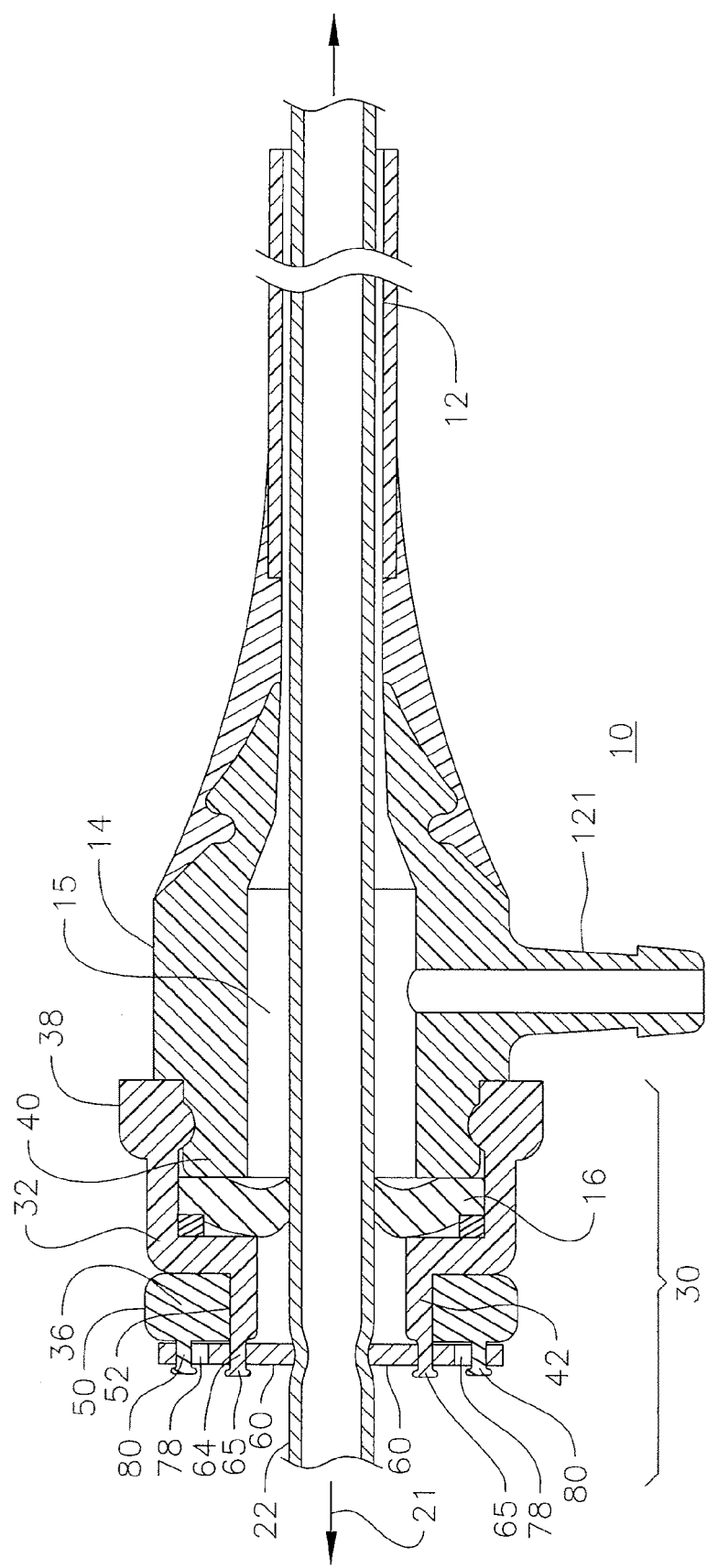

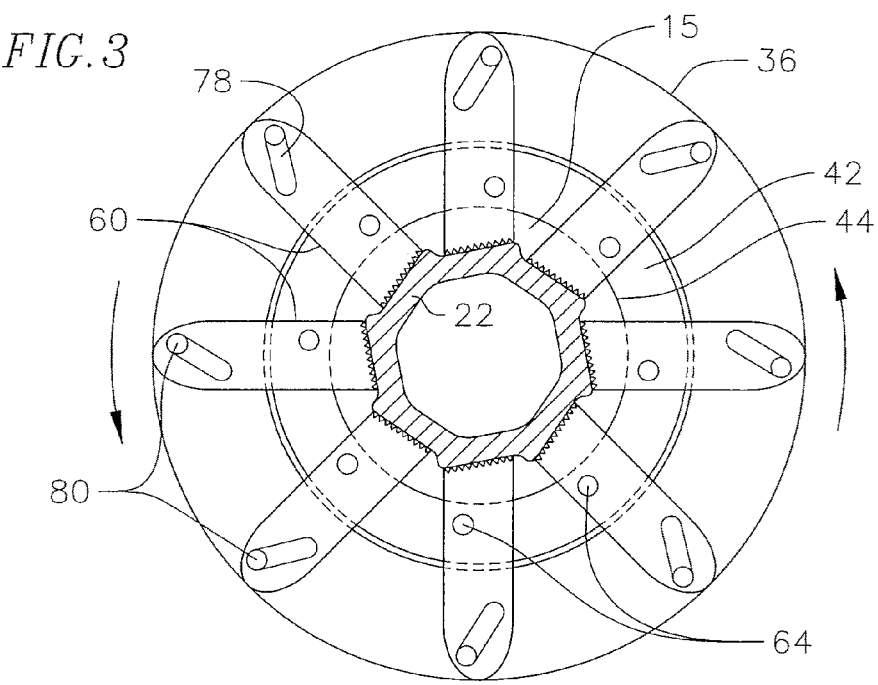
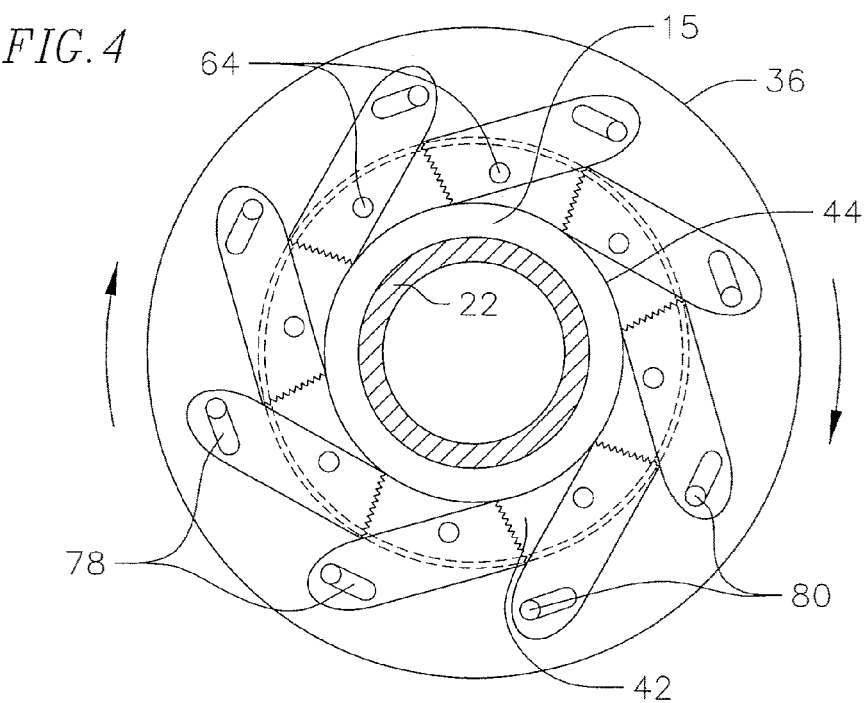

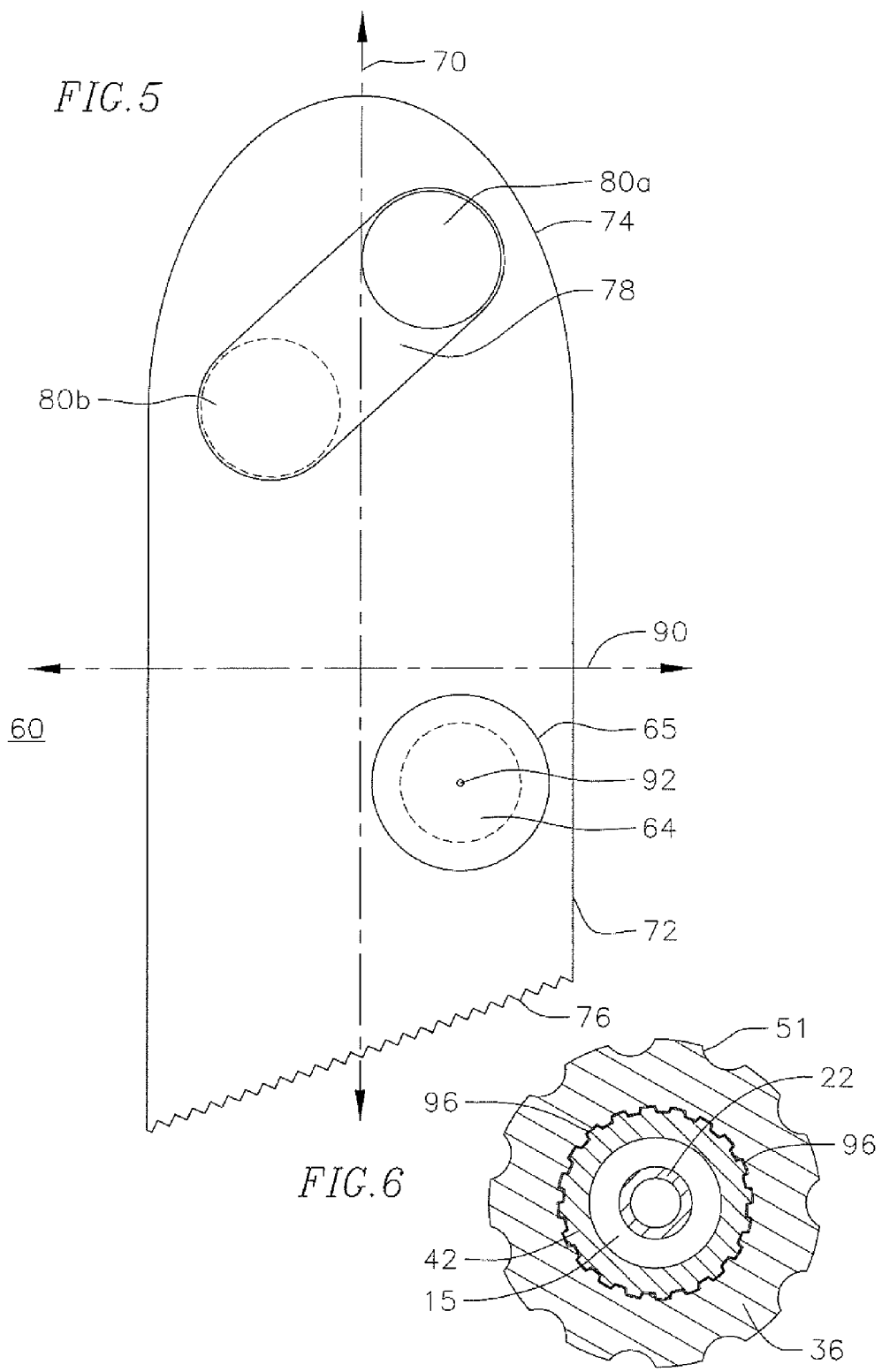

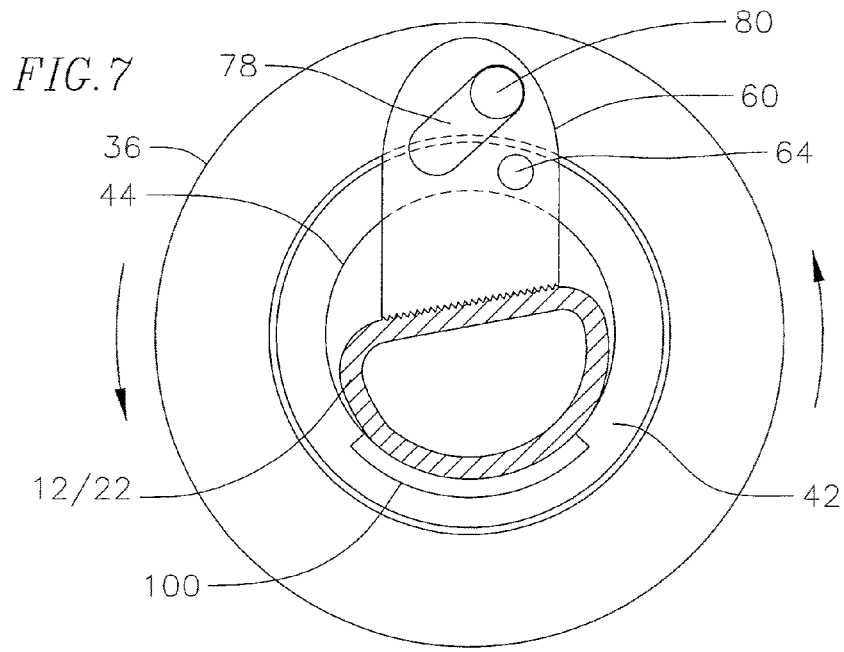
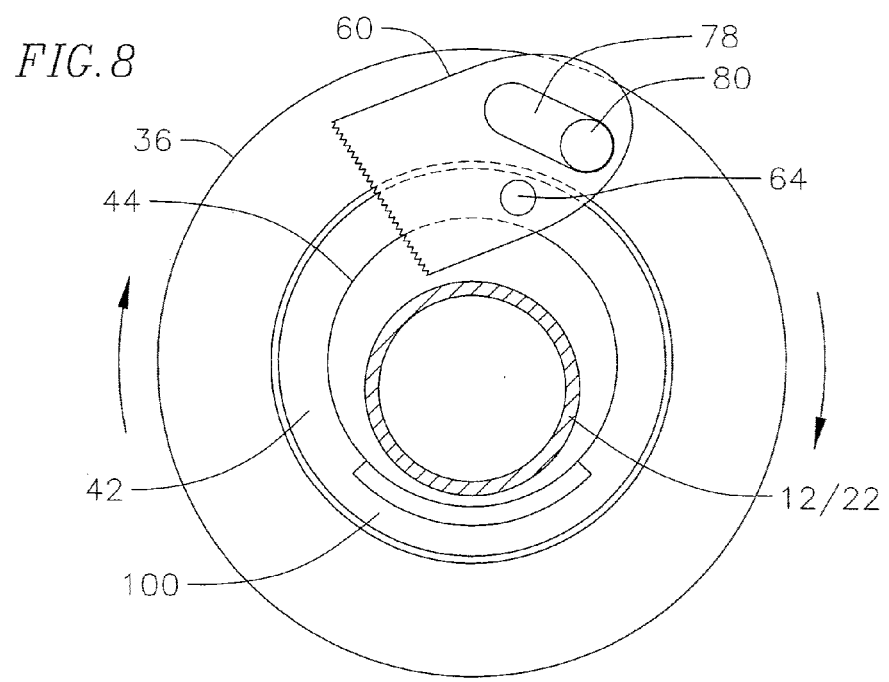

CATHETER SHEATH INTRODUCER WITH ROTATIONAL LOCK

FIELD OF INVENTION

The present invention relates to an improved catheter sheath introducer.

BACKGROUND OF INVENTION

Catheter sheath introducers are well known in the health care industry as a means of providing access to the circulatory system for a number of applications. In a now well know process, the catheter sheath introducer is placed in a desired blood vessel to facilitate various procedures. Among these medical procedures are mapping and ablation of the heart, balloon angioplasty and the like which require the manipulation and deflection of a long catheter through the circulatory system to reach the heart or other target sites within the patient's body. In some cases, the manipulation and deflection of the catheter are achieved by manipulation and deflection of the sheath introducer. And, if a catheter is not secured within the sheath introducer, it may move during manipulation of the sheath introducer making it difficult to accurately place and position the catheter's distal tip.

Sheath introducers have small parts and thus offer little space and surface on which to provide additional mechanism or means to lock the catheter relative to the sheath introducer. But, by locking the catheter in the introducer, the catheter can be more easily maneuvered in the heart chamber or elsewhere in the body via manipulation and deflection of the sheath introducer. Thus, it is desirable for an improved catheter sheath introducer that can readily lock and release a catheter without significantly increasing the bulk or size of the sheath introducer or interfering with the operation of the sheath introducer or the catheter extending therethough.

SUMMARY OF THE INVENTION

The present invention is directed to a sheath introducer for use with a catheter, having a hub, a flexible tube adapted for insertion into a patient, and a lock assembly that can grip or release the catheter upon rotation of a user interface without intefering with the operation of the introducer or the catheter.

In one embodiment, the sheath introducer includes a hub with an opening at one end and a flexible tube at the other end, where the opening leads to a lumen that extends through the hub and the tube which receive the catheter. The lock assembly includes a rotational knob and a plurality of prongs or fingers arranged in a radial pattern around the opening wherein the prongs are actuated simultaneously to open or close on the catheter in response to the bi-directional rotational of the knob.

In a more detailed embodiment, the sheath introducer includes an end cap with a neck portion circumscribing the opening of the hub. The rotational knob has a central hole through which neck portion protrudes so that the rotational knob is a circumferential relation to the neck portion. Pins projecting from the neck portion serve as individual rotational axes for the prongs which are in a radial pattern around the opening. Each prong has a contact end and a cam portion, wherein the contact end is rotated by the cam portion in response to the rotational knob either inwardly toward the center of the hub opening to close on the catheter or outwardly away from the center to release the catheter.

In a more detailed embodiment, the cam portion of each prong is formed with an aperture that receives a respective cam pin extending from the knob, so that rotational motion of the knob is coupled to rotational motion of each prong simultaneously and synchronously. The axis of rotation of each prong and the alignment of each aperture can be varied for different rotational motion and/or degree of compression and friction between the catheter and the contact end of each prong. In one detailed embodiment, the axis of rotation is off center and the aperture is off angle.

In another more detailed embodiment, the plurality of prongs ranges between about two and ten, preferably between four and eight, and the prongs are equidistance from each other around the opening.

BRIEF DESCRIPTION OF THE DRAWINGS

These and other features and advantages of the present invention will be better understood by reference to the following detailed description when considered in conjunction with the accompanying drawings wherein:

FIG. 2 is a side cross-sectional view of the sheath introducer of FIG. 1;

FIG. 3 is an end view of an embodiment of a sheath introducer of the present invention in a closed configuration;

FIG. 4 is an end view of the sheath introducer of FIG. 3 in an open configuration;

FIG. 5 is a front view of an embodiment of a prong of the present invention; and FIG. 6 is a cross-sectional view of the sheath introducer of FIG. 1, taken along line 6-6.

FIG. 7 is an end view of an alternate embodiment of a sheath introducer of the present invention in a closed configuration;

FIG. 8 is an end view of the sheath introducer of FIG. 7 in an open configuration;

DETAILED DESCRIPTION OF THE INVENTION

Figure 1:
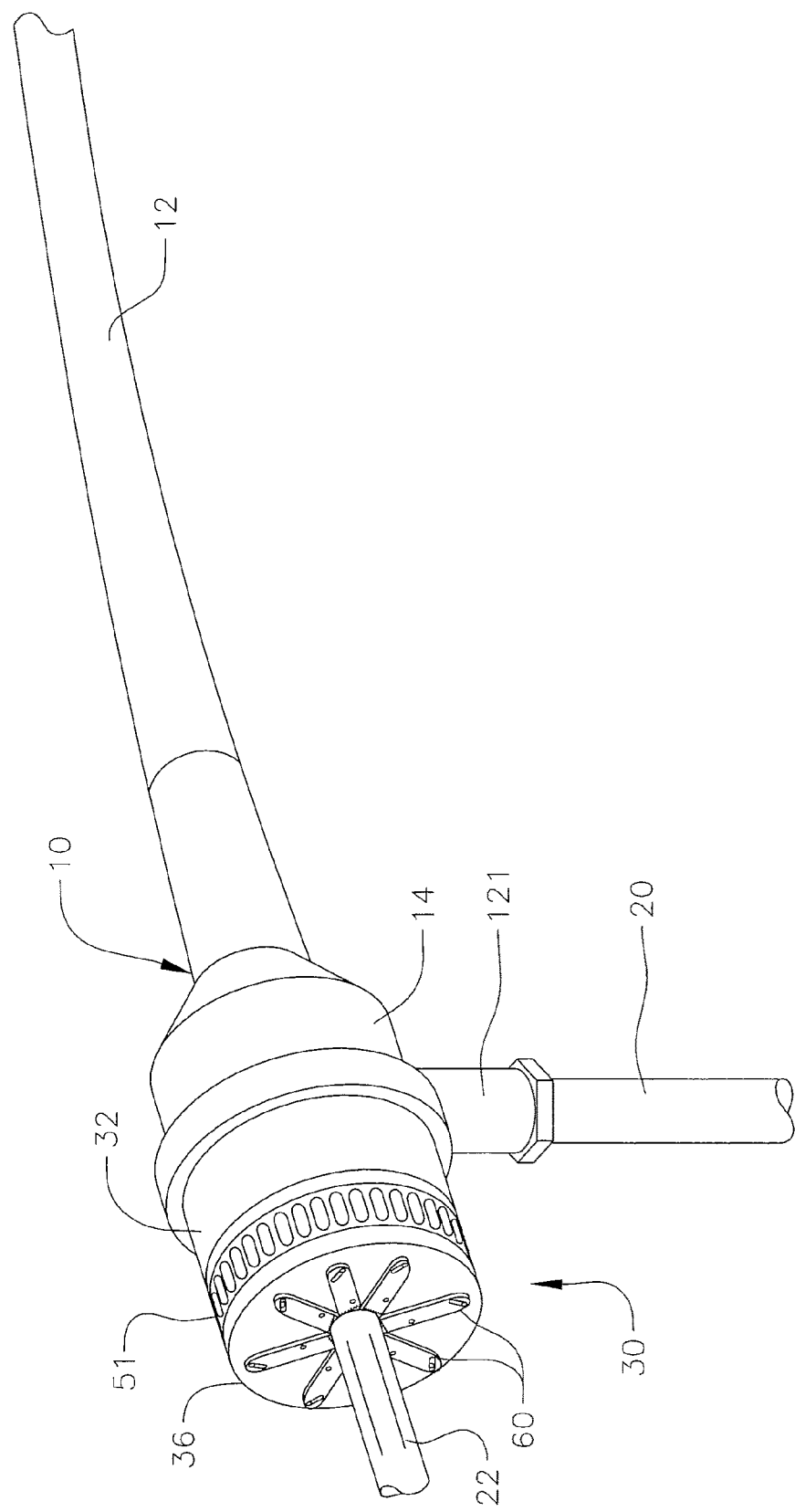
FIG. 1 is a side view of an embodiment of a sheath introducer of the present invention in use with a catheter.

FIGS. 1 and 2 show an embodiment of a catheter sheath introducer 10 having a hub 14 and a tubular sheath 12 attached to the distal end of hub 14. The sheath introducer includes a hemostasis valve 16 to provide sealing of the sheath 12 around a catheter tubular body 22 that extends along a longitudinal axis 21 of the sheath introducer through a central lumen 15 that extends through the hub 14 and the sheath 12. A branch conduit 20 and a locking sleeve 121 off of hub 14 are provided to allow for, among other things, connections to saline solution or medicines and access to other medical procedures. It is understood that a guide wire may also extended through the sheath introducer as it is often used with catheters. Sheath introducers are described in U.S. Pat. No. 5,807,350, the entire content of which is hereby incorporated by reference.

Mounted proximally of the hub is a releasable rotational lock assembly 30 that includes an end cap 32 and a user interface 34. In the illustrated embodiment, the user interface includes a knob 36. The end cap 32 is provided at the proximal end of hub 14 to cover and secure the hemostatsis valve 16. The end cap 32 has a distal portion 38 that snap fits with a proximal circumferential portion 40 of the hub 14. The end cap 32 at its proximal end is configured with a neck portion 42 that defines an axial opening 44 leading to the central lumen 15 of the sheath introducer 10. Mounted on the neck portion 42, the knob 36 is shaped as a disc with a circumferential edge 50, with an outer diameter generally equal to that of the end cap 32. The knob 36 has a central hole 52 that receives the neck portion 42 of the end cap 32 and allows the knob 36 to be bi-directionally rotatable and adjustable about the longitudinal axis 21 of the introducer 10. The circumferential edge 50 which is grasped by fingers of the user may be formed with a friction-inducing surface 51.

As also shown in FIGS. 3 and 4, the rotational lock assembly 30 further includes a plurality of locking members or prongs 60 mounted on a proximal face of the end cap 32 that are adapted to contact and grip the catheter tubular body 22 extending through the introducer 10 when the knob 36 is rotated in one direction (FIG. 3) and to release the tubular body 22 when the knob 36 is rotated in the other direction (FIG. 4). Arranged in a radial pattern generally equidistant and equiangular to each other around the opening 44 to the central lumen 15, the prongs 60 are each fixedly but rotationally or pivotally (used interchangeably herein) mounted on a respective pin 64 formed as a projection from a proximal end of the neck portion 42. The pins 64 are thus also generally equidistant and equiangular about the opening 44. The pins 64 extend parallel to the longitudinal axis 21 of the introducer 10. A proximal end of each pin has a head 65 which retains the prong 60 on the pin 64, and in turn, the knob 36 on the neck portion 42 of the hub 14.

In the illustrated embodiment, as best seen in FIG. 5, each prong 60 is elongated along its longitudinal axis 70 which intersects a center of the opening 44. The prong 60 flares or widens toward the opening 44, having a wider contact end 72 that is directed inwardly toward the opening and a narrower cam portion 74 that is directed outwardly away from the opening. Each contact end 72 has a friction-inducing surface 76 adapted to grip the catheter tubular body 22. The contact end can be a straight edge or a curved edge, e.g., with a concave or convex curvature, as desired.

Each cam portion 74 is configured with an aperture 78 through which a respective cam actuator or pin 80 formed as a projection extending from a proximal face of the knob 36 engages the cam portion 74 of the prong 60 in coupling rotational motion of the knob 36 and rotational motion of each of the prongs 60. The projection pin 64 of the neck portion 42 of the hub extends through the prong 60 at a location that is off center from the longitudinal axis 70 and/or the mid-axis 90 and closer to the contact end 72 where the pin 64 defines a rotational axis 92 of the prong about the pin 64 that is generally parallel to the longitudinal axis 21 of the hub. The cam aperture 78 is elongated, more oval than circular, and is aligned off angle, for example, angled counterclockwise relative to the longitudinal axis 70; however, it is understood that the cam aperture can be canted either clockwise or counterclockwise and configured in any variety of shapes as needed or desired. As such, clockwise rotation of the knob 36 opens the rotational lock assembly 30 by simultaneously rotating each of the cam actuators 80 clockwise which rotate the prongs 60 about their axes 92 clockwise until the cam actuators 80 engage the cam apertures 78 in the position 80b (FIGS. 4 and 5) thus pivoting open the prongs 60 so that the contact ends 72 sweep outwardly away from the opening and release the tubular body 22. Likewise, counterclockwise rotation of the knob 36 closes or actuates the assembly 30 by simultaneously rotating each of the cam actuators 80 counterclockwise which rotates the prongs 60 about their axes 92 counterclockwise until the cam actuators 80 engage the cam apertures 78 in the position 80a (FIG. 3) thus pivoting closed the prongs 60 so that the contact ends 72 sweep inwardly toward the opening and the surface 76 to grip and compress the tubular body 22.

Figure 10:
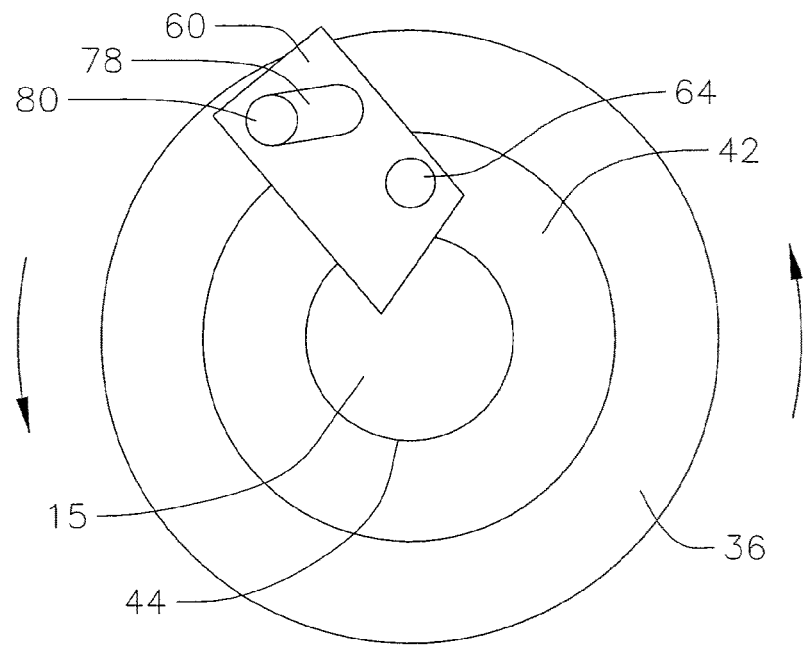
FIG. 10 is an end view of another alternate embodiment of a sheath introducer of the present invention in a closed configuration.
Figure 11:
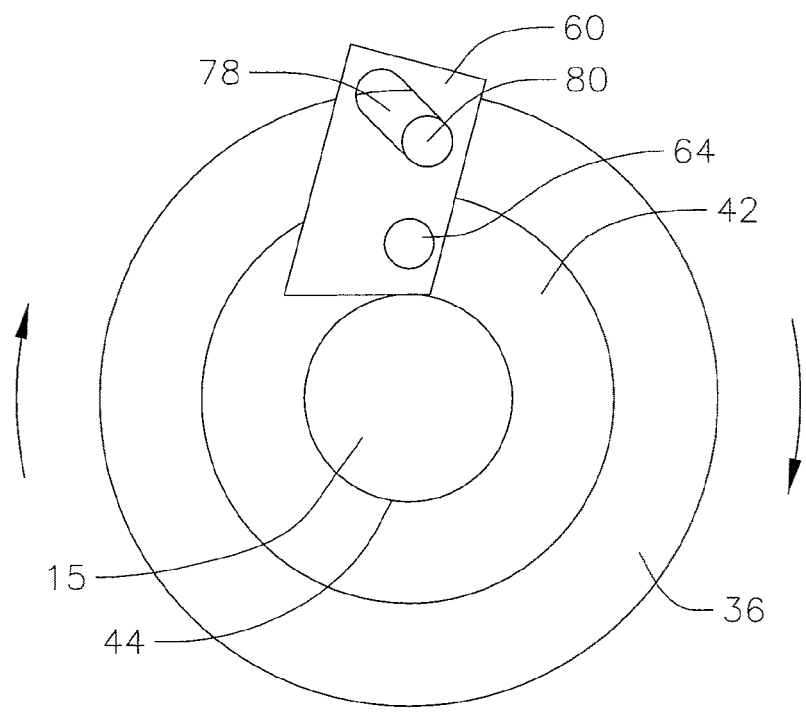
FIG. 11 is an end view of the sheath introducer of FIG. 10 in an open configuration.

As understood by one of ordinary skill in the art, various factors, including the relative size, configuration and orientation of the prongs, the aperture, the cam pins and the projection pins determine the interaction of these parts, including the type and/or size (french) of the catheter body that can be used with the sheath introducer. FIGS. 10 and 11 show an alternate embodiment of the prongs 60, for example, as being more rectangular with four corners, one of which is adapted to close in on the opening 44 to contact the catheter tubular body (not shown) when the knob 36 is rotated in the counterclockwise direction, and to swing away from the opening 44 when the knob 36 is rotated in the clockwise direction. Also in this embodiment, the aperture 78 is off angle and canted counterclockwise. The rotational lock assembly can be alternately configured so that it operations in reverse, that is, it locks on the tubular body when it is rotated clockwise and unlocks when it is rotated counterclockwise. These factors also determine the amount of compression around the catheter body in the recognition that such that a sufficient amount of frictional force applied by the contact end on the catheter body allows for the knob to stay in place until rotated or otherwise adjusted by the user. In that regard, friction-inducing surfaces can be provided on an inner circumferential surface of the knob 36 and the outer circumferential surface of the neck portion 42 of the hub. For example, interfacing ridges 96 (FIG. 6) extending in the longitudinal direction can provide locking incremental rotational adjustment in either clockwise or counterclockwise directions.

The present sheath introducer includes at least two prongs, preferably equidistance apart and diametrically opposing each other across the opening. The number of prongs can range between about two and ten, more preferably between four and eight.

In alternate embodiment, the lock assembly 30 employs a single prong 60. As illustrated in FIGS. 7 and 8, the single prong 60 is of a larger size and it acts in conjunction with a cradle 100 that projects from the neck portion 42 to oppose the prong 60 from across the opening 44. The cradle projects in the direction of the longitudinal axis 21 and has a curved, or semi-circular cross-section so that it serves as an abutment against which the catheter tubular body 22 is compressed by the prong 60. It is understood that a lesser plurality of prongs can be employed in this embodiment, for example, ranging between about one to four.

Figure 9:
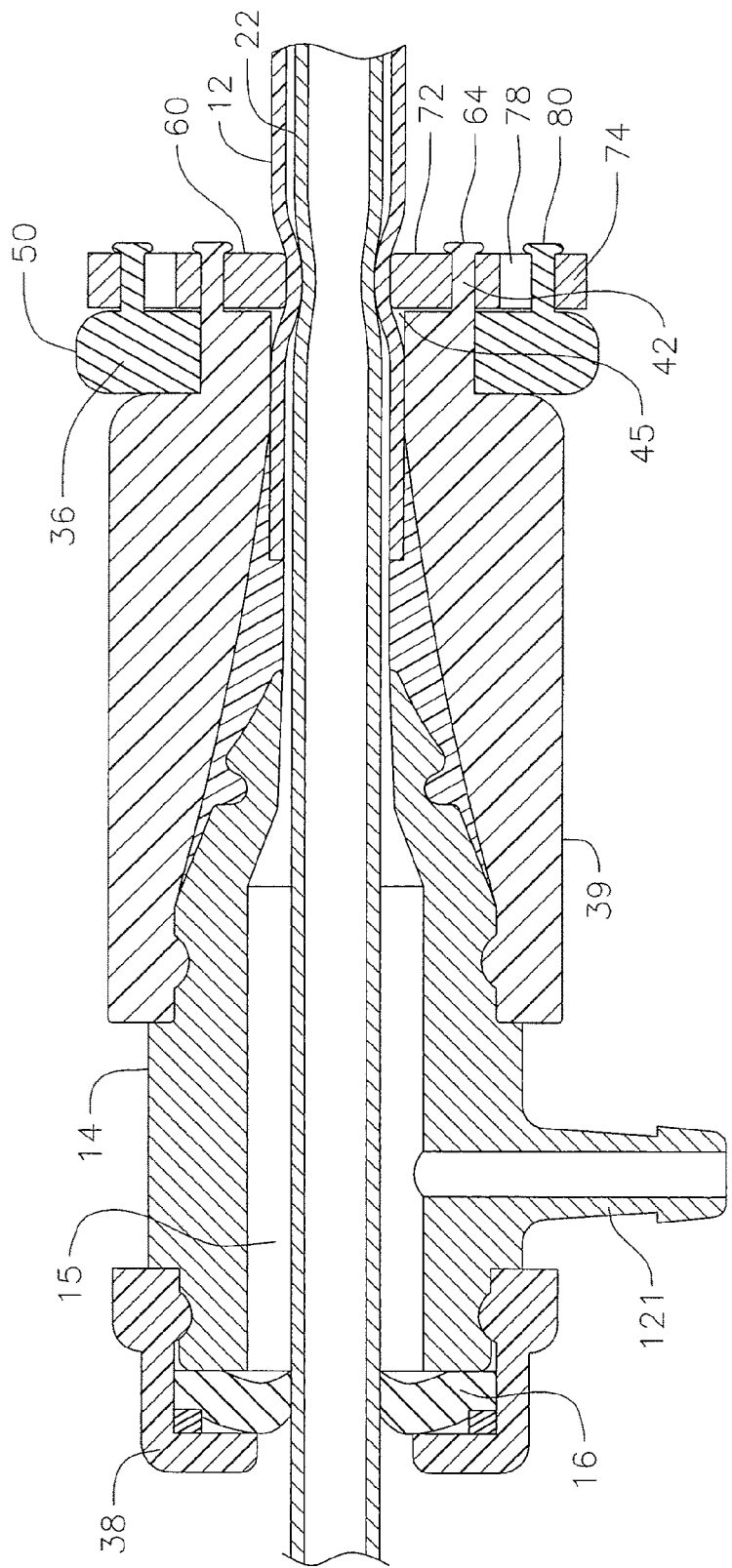
FIG. 9 is a side-cross sectional view of another alternate embodiment of a sheath introducer of the present invention.

FIG. 9 illustrates another alternate embodiment of the sheath introducer which includes many similarities to the aforementioned embodiment. Differences between the two embodiments include a front cap 39 that is mounted on the proximal end of the hub 14 and a proximal portion of the tubular sheath 12, where a neck portion 42 extends from a distal face of the front cap 39 and defines a distal axial opening 45 in communication with the central lumen 15. The locking assembly 30 is thus mounted distally of the hub 14, and the prongs 60 act on the catheter tubular body 22 through the tubular sheath 12 instead of gripping the tubular body 22 directly. In this embodiment, the plurality of prongs 60 may be less and/or gap or spacing between the prongs may be greater so that the sheath 12 can deform under compression. To that end, the sheath 12, or at least the portion of the sheath being compressed, has a sufficiently flexible and elastic construction such that it can be deformed by the prongs 60 without causing unrecoverable or permanent deformation.

It is understood by one of ordinary skill in the art that the lock assembly can be distal or proximal of the hub, and can in fact mounted on or be part of the hub. It is also understood by one of ordinary skill in the art that the prongs 60 can face proximally or distally so long that they act on and compress the catheter tubing 22 either directly or indirectly via the sheath 12. In that regard, it is understood that the embodiment of FIGS. 7 and 8 can also be positioned distal the hub 14 and/or the front cap 39 such that the single prong 60 contacts and compresses the sheath 12 to act on and compress the catheter tubular body 22 extending therethough.

The preceding description has been presented with reference to certain exemplary embodiments of the invention. Workers skilled in the art and technology to which this invention pertains will appreciate that alterations and changes to the described structure may be practiced without meaningfully departing from the principal, spirit and scope of this invention. It is understood that the drawings are not necessarily to scale. Accordingly, the foregoing description should not be read as pertaining only to the precise structures described and illustrated in the accompanying drawings. Rather, it should be read as consistent with and as support for the following claims which are to have their fullest and fairest scope.

What is claimed is:

1. A sheath introducer for use with a catheter, comprising:
a hub having a proximal end and a distal end,
a flexible tube extending from the distal end, the flexible tube adapted for insertion into a patient;
an opening that communicates with a lumen extending through the hub and the flexible tube, the lumen adapted to receive the catheter; and
a lock assembly having a rotational member and at least one prong having a long dimension and a short dimension, wherein the at least one prong comprises a cam portion responsive to rotation of the rotational member and the short dimension defining an end contact portion adapted to contact a portion of the catheter when the rotational member is rotated in one direction and to release the portion of the catheter when the rotational member is rotated in another direction, the cam portion of the at least one prong comprising an elongated cam aperture for receiving a cam actuator extending from the rotational member, the cam actuator being translationally moveable within the elongated cam aperture in response to rotation of the rotational member, and wherein upon rotating the rotational member to contact or release the portion of the catheter, the at least one prong is rotated without rotation of the flexible tube.

2. A sheath introducer of claim 1, wherein the at least one prong comprises a plurality of prongs arranged in a radial pattern around the opening.

3. A sheath introducer of claim 2, wherein the plurality of prongs comprises between about two and ten prongs.

4. A sheath introducer of claim 2, wherein the plurality of prongs comprises between about four and eight prongs.

5. A sheath introducer of claim 2, wherein the plurality of prongs are generally equidistant from each other about the opening.

6. A sheath introducer of claim 1, wherein each prong is adapted to rotate when actuated by the rotational member.

7. A sheath introducer of claim 6, wherein each prong is adapted to rotate about a respective off center axis.

8. A sheath introducer of claim 1, where the elongated cam aperture is off angle.

9. A sheath introducer of claim 1, wherein the contact portion of each prong has a contact end configured to grip the catheter.

10. A sheath introducer of claim 1, wherein the lock assembly further comprises a cradle generally opposing the at least one prong from across the opening.

11. A sheath introducer of claim 1, wherein when the end contact portion of the at least one prong contacts the portion of the catheter, the cam actuator engages the elongated cam aperture at a first position within the elongated cam aperture, and when the end contact portion of the at least one prong releases the portion of the catheter, the cam actuator engages the elongated cam aperture at a second position within the elongated cam aperture different from the first position.

12. A sheath introducer for use with a catheter, comprising:
a hub having a proximal end and a distal end,
a flexible tube extending from the distal end, the flexible tube adapted for insertion into a patient;
a lumen extending through the hub and the flexible tube;
a valve proximal of the flexible tube;
an end cap mounted over the valve onto the proximal end, the end cap having a neck portion with pins extending therefrom; and
a lock assembly comprising a rotational member mounted on the neck portion, and a plurality of prongs rotationally mounted on the pins and rotationally coupled to the rotational member, each of the prongs having a long dimension and a short dimension, wherein each prong comprises a cam portion responsive to rotation of the rotational member and the short dimension of the prong defining an end contact portion adapted to compress a portion of the catheter when the rotational member is rotated in one direction and to release the portion of the catheter when the rotational member is rotated in another direction, wherein the cam portion of each of the prongs comprises an elongated cam aperture for receiving a cam actuator extending from the rotational member, the cam actuator being translationally moveable within the elongated cam aperture in response to rotation of the rotational member, and wherein upon rotating the rotational member to compress or release the portion of the catheter, the prongs are rotated without rotation of the flexible tube.

13. A sheath introducer of claim 12, wherein the prongs simultaneously rotate in response to rotation of the rotational member by a user.

14. A sheath introducer of claim 12, wherein contacting surfaces between the rotational member and the neck portion are friction-inducing.

15. A sheath introducer of claim 12, wherein when the end contact portion of each of the prongs compresses the portion of the catheter, the cam actuator engages the elongated cam aperture at a first position within the elongated cam aperture, and when the end contact portion of each of the prongs releases the portion of the catheter, the cam actuator engages the elongated cam aperture at a second position within the elongated cam aperture different from the first position.

16. A sheath introducer for use with a catheter, comprising:
a hub having a proximal end and a distal end,
a flexible tube extending from the distal end, the flexible tube adapted for insertion into a patient;
a lumen extending through the hub and the flexible tube;
an end cap mounted on the hub, the end cap defining an opening for the lumen; and
a lock assembly having a rotational member mounted on the end cap, and a plurality of prongs mounted on the end cap, each of the plurality of prongs being rotatable about a respective rotational axis, and each of the plurality of prongs having a long dimension and a short dimension, wherein each prong comprises a cam portion responsive to rotation of the rotational member, and the short dimension of the prong defining an end contact portion, the cam portion of each prong having an elongated cam aperture, wherein the rotational member has a cam pin for each of the plurality of prongs, each cam pin being translationally moveable within the elongated cam aperture of the respective prong in response to rotation of the rotational member and adapted to rotate the respective prong in response to rotation of the rotational member by a user so that the end contact portion of the respective prong compresses a portion of the catheter when the rotational member is rotated in one direction and releases the portion of the catheter when the rotational member is rotated in another direction, and wherein upon rotating the rotational member to compress or release the portion of the catheter, the plurality of prongs are rotated without rotation of the flexible tube.

17. A sheath introducer of claim 16, wherein the plurality of prongs are mounted in a radial pattern around the opening.

18. A sheath introducer of claim 16, wherein the rotational axis of each prong is off center.

19. A sheath introducer of claim 16, wherein the hub has a neck portion on which the rotational member is mounted.

20. A sheath introducer of claim 16, wherein when the end contact portion of the respective prong compresses the portion of the catheter, the cam pin engages the elongated cam aperture of the respective prong in a first position within the elongated cam aperture, and when the end contact portion of the respective prong releases the portion of the catheter, the cam pin engages the elongated cam aperture of the respective prong in a second position within the cam aperture different from the first position.

* * * * *